United States Patent
Mailland

(10) Patent No.: US 7,033,578 B2
(45) Date of Patent: Apr. 25, 2006

(54) ANTIMYCOTIC NAIL VARNISH COMPOSITION

(75) Inventor: Federico Mailland, Milan (IT)

(73) Assignee: Polichem S.A., Luxembourg (LU)

( * ) Notice: Subject to any disclaimer, the term of this patent is extended or adjusted under 35 U.S.C. 154(b) by 0 days.

(21) Appl. No.: 10/297,345

(22) PCT Filed: Jul. 18, 2001

(86) PCT No.: PCT/EP01/08311

§ 371 (c)(1), (2), (4) Date: Jun. 23, 2003

(87) PCT Pub. No.: WO02/07683

PCT Pub. Date: Jan. 31, 2002

(65) Prior Publication Data

US 2004/0022831 A1    Feb. 5, 2004

(30) Foreign Application Priority Data

Jul. 24, 2000  (DE) ............................... 100 35 991

(51) Int. Cl.
*A61K 7/04* (2006.01)

(52) U.S. Cl. .................. 424/61; 424/401; 424/404; 514/55; 514/777; 514/781

(58) Field of Classification Search ............... 424/401, 424/404, 61; 514/777, 781, 55
See application file for complete search history.

(56) References Cited

U.S. PATENT DOCUMENTS

| | | | | |
|---|---|---|---|---|
| 4,946,870 A | * | 8/1990 | Partain et al. | 514/777 |
| 4,954,619 A | * | 9/1990 | Lang et al. | 536/20 |
| 5,346,692 A | | 9/1994 | Wohlrab et al. | 424/61 |
| 5,681,849 A | | 10/1997 | Richter et al. | 514/481 |
| 5,856,355 A | | 1/1999 | Richter et al. | 514/481 |
| 6,005,001 A | | 12/1999 | Richter et al. | 514/481 |
| 6,121,314 A | | 9/2000 | Richter et al. | 514/481 |
| 6,231,875 B1 | | 5/2001 | Sun et al. | |
| 6,562,802 B1 | | 5/2003 | Johansson et al. | |

FOREIGN PATENT DOCUMENTS

| | | |
|---|---|---|
| CA | 2 326 774 A1 | 7/1999 |
| DE | 39 03 797 A1 | 8/1990 |
| DE | 42 15 677 A1 | 11/1992 |
| DE | 36 87 458 T2 | 7/1993 |
| DE | 42 12 105 A1 | 10/1993 |
| DE | 199 22 230 A1 | 11/2000 |
| EP | 0 368 253 A2 | 11/1989 |
| EP | 0 515 310 A1 | 5/1992 |
| EP | 0 515 312 A2 | 11/1992 |
| EP | 0 247 142 B1 | 1/1993 |
| EP | 0 985 408 A2 | 9/1999 |
| JP | 05339152 A | 12/1993 |
| WO | WO 98/26788 | 6/1998 |

OTHER PUBLICATIONS

Baba et al. Antifungal acticity of aqueous soluble chitosan derivatives on Fusarium and verticillium. Nippon Kagaku kaishi 1996, vol. 1, pp. 48-53.*

Knapczyk et al., *Simple Tests Demonstrating the Antimycotic Effect of Chitosan*, International Journal of Pharmaceutics, 80, pp. 33-38, (1992).

Knapczyk, Jan, *Antimycotic Buccal And Vaginal Tablets with Chitosan*, International Journal of Pharmaceutics, 88, pp. 9-14, (1992).

JP 59007117 (1984) Abstract.

Abstract-Knapczyk, J.-"Preclinical study of antimycotic chitosan hydrogel efficacy", Chitin World, 6th, 1994, 504-511.

JP 1994-0156484 (1994) Abstract.

International Search Report for PCT/EP01/08311.

* cited by examiner

*Primary Examiner*—Thurman K. Page
*Assistant Examiner*—Lakshmi Channavajjala
(74) *Attorney, Agent, or Firm*—Kilyk Bowersox, P.L.L.C.

(57) ABSTRACT

The present invention relates to a composition comprising a) at least one antimycotic agent and b) at least one film forming agent wherein component b) is a derivative of chitosan selected from hydroxyalkylchitosans and carboxyalkylchitosans and its use as a nail varnish. The present invention is further directed to the use of a water soluble film forming agent selected from hydroxyalkylchitosans and carboxyalkylchitosans as an additive in a nail varnish.

19 Claims, No Drawings

ANTIMYCOTIC NAIL VARNISH COMPOSITION

This application claims the benefit of earlier filed International Application No. PCT/EP01/08311 filed Jul. 18, 2001.

The present invention relates to a composition comprising at least one antimycotic agent and at least one film forming agent and its use as a nail varnish. The present invention is further directed to the use of a water soluble film forming agent as an additive in a nail varnish.

Mycosis of the nail and nail connections (onychomycosis) is a widespread disease and can, in many cases, not be satisfactorily remedied. Onychomycosis is frequently caused by dermatophytes but may also be caused by yeasts and Candida. It includes dermatophyte infections of the nail plate as well as infections of nails by any fungus, including yeast or molds. The most common causes of dermatophyte infections of the nails are *Trichophyton rubrum, T. mentagrophytes* and *Epidermophyton floccosum.*

The development of onychomycosis is promoted by circulatory disturbances, hyperhidrosis, wearing rubber gloves or rubber soles, manicure injuries and frequent contact with water and soaps. Commonly affected occupational groups include sportsmen and people working in the medical field.

Possible modes of treatment of onychomycosis include systemic treatment whereby the antimycotic agent is orally applied, surgical or a chemical treatment of the affected nails as well as topical treatment of the nails whereby the antimycotic agent is applied locally on the nails. Topical treatments have been favored over other modes since they are not as aggressive, do not possess so many side effects and act locally on the nails.

A number of compositions for topical application of the active agent has been previously suggested. For example, in WO 00/15202, topical application products for nails which may be used for the treatment of onychomycosis are disclosed. The product is free of water and contains one or more active agent, a $C_1$ to $C_4$-alkyl ester of lactic acid, tartaric acid or citric acid as a carrier and optionally physiologically acceptable auxiliaries. The preferred topical form of administration are solutions but tinctures, emulsions, gels, creams and paste are also possible.

Another mode of a topical administration which has been recently proposed is to include the antimycotic agent in a nail varnish which is then applied on the nails and nail connections. In early compositions, problems arose that severe onychomycosis could not be treated effectively which was probably due to an insufficient bioavailability of the active agent after the varnish had dried and formed a solid composition.

More recently, nail lacquers or nail varnishes have been proposed which are attempting to overcome the above problems. For example, WO 99/39680 discloses an antifungal nail lacquer. This lacquer is suitable for the treatment of onychomycosis and comprises effective amounts of ciclopirox and pharmaceutically acceptable salts thereof. The lacquer is characterized by a water insoluble film forming polymer which protects the treated nail by the formation of a hard, clear and water resistant film. Similarly, in EP-A-226984 an antimycotic nail varnish is described containing a 1-hydroxy-2-pyridone, e.g. ciclopirox olamine, in combination with a water insoluble film forming agent, and a physiologically acceptable solvent and additives customary in cosmetics.

Although these conventional nail varnishes may be suitable in preventing and treating mycosis of nails and nail connections, they possess certain dermatological and aesthetic disadvantages. For example, when the lacquer is applied it may burn, in particular when applied on the periungueal bed. For removal of the varnish or lacquer, organic solvents have to be used which may have a negative effect on the exposed adjacent skin. Therefore, these nail varnishes may not be suitable for patients with sensitive skin. Moreover, the nail varnish results in a glossy, sticky and shiny film which may not be agreeable to all mycosis patients. Due to their glossy nature, commercial antimycotic nail lacquers also tend to splint easily. In addition, traditional nail lacquer formulations are, due to the nature of their components, impermeable to moisture and air. This leads to an occlusive medication which is not desirable in the treatment of mycoses.

It is therefore the object of the present invention to provide a nail varnish composition which overcomes the above noted disadvantages, which can be easily formulated, prepared and stored and provides good antimycotic effects.

This object is achieved by a composition comprising
  a) at least one antimycotic agent and
  b) at least one water soluble film forming agent.

Moreover, the present invention is directed to the use of said composition as a nail varnish.

The present invention is also directed to the use of a water soluble film forming agent as an additive in a nail varnish.

The composition in accordance with the present invention comprises as a component a) at least one antimycotic agent. The antimycotic agent may be selected from any known antimycotic agent of synthetic or natural origin. The active agent may be in the free form, i.e. as the free acid or base, or in the form of its salts. Examples include:

1-hydroxy-2-pyridone compounds and their salts, e.g. ciclopirox, rilopirox, piroctone, ciclopirox olamine and the 1-hydroxy-2-pyridone compounds disclosed in U.S. Pat. No. 4,957,730;

imidazole derivatives and their salts, e.g. Clotrimazole, Econazole, Isoconazole, Ketoconazole, Miconazole, Tioconazole, Bifonazole, Fenticonazole and Oxiconazole;

polyene derivatives and their salts, e.g. Nystatin, Natamycin and Amphotericin;

allylamine derivatives and their salts, e.g. Naphtifine and Terbinafine;

triazole derivatives and their salts, e.g. Fluconazole, Itraconazole, Terconazole and Voriconazole;

morpholine derivatives and their salts, e.g. Amorolfine and morpholines disclosed in U.S. Pat. No. 5,120,530;

griseofulvin and related compounds, e.g. griseofulvin;

acidic compounds, e.g. undecylenic acid and its salts, in particular, the zinc and calcium salts of undecylenic acid;

tolnaphtate and its salts; and flucytosine and its salts.

The antimycotic agent is preferably selected from 1-hydroxy-2-pyridone compounds and their salts.

The antimycotic agent may also be selected from natural sources, in particular plant extracts. Examples of these extracts include tea tree oil (*Melaleuca alternifolia*), lavender oil (*Lavandula officinalis chaix*) and the leaf extract of the neem tree (*Azadirachta indica*).

The antimycotic agent may be used alone or in combination with other antimycotic agents. In particular, if the antimycotic agent is of natural origin, it is preferred to use it in combination. A preferred mixture is a combination of tea tree oil, lavender oil and the leaf extract of the neem tree.

The amount of the antimycotic agent (component a)) will vary depending on its structure and its antimicrobial activity, the release rate from the film, the diffusion characteristics and the penetration behavior in the nail. In general, an effective amount of the antimycotic agent, i.e. an amount which is effective to kill the infecting microorganism, which will generally be several to several tens to hundreds of times greater than the mean inhibitory concentration (MIC), may be employed in the composition in accordance with the present invention. Thus, it is preferred that the amount of component a) is in the range of 0.1 to 15 wt. %, more preferably 0.3 to 15 wt. %, most preferably 0.5 to 10 wt. % by weight of the total composition.

The composition in accordance with the present invention also comprises as a component b) at least one water soluble film forming agent. The water soluble film forming agent may be selected from any water soluble film forming agent known in the art. Film forming agents are by definition (see e.g. DIN 55945 (12/1988)) components of a binder which are essential for forming a film, i.e. a thin layer or cover.

The term "water soluble" means in this context that the film forming agent is fully compatible with water so that at 20° C. one part of the film forming agent is soluble in 100 parts or less, preferably 50 parts or less, more preferably 30 parts or less, most preferably 10 parts or less of water.

Due to the presence of a water soluble film forming agent the use of a wide variety of solvents is possible, ensuring, thus, an easy application of the drug and simplifying also the storage of the formulation. Since the film forming agent may be used in combination with a wide variety of solvents, the formulations can be chosen so that the nail varnish composition in accordance with the present invention does not burn, is easily removable without the use of organic solvents and can be applied to the periungueal bed where the multiplication of fungal cells is favored by the presence of the hyphae. The composition in accordance with the present invention is therefore suitable as a nail varnish even if the patient suffers from sensitive skin which may react adversely to certain organic solvents. Furthermore, the water soluble film forming agent when used in the composition in accordance with the present invention provides a non-glossy, non-sticky and very plastic film which possesses a matte and natural look favored by the majority of mycosis patients. As a further advantage, the claimed composition when used as a nail varnish is permeable to moisture and air providing, thus, an effective tool to treat mycoses.

As the film forming agent used in accordance with the present invention typically macromolecular compounds of synthetic or natural origin can be used which are water soluble or have been derivatized by functional groups in order to impart water solubility. Preferably, water soluble derivatives of naturally occurring polymers or derivatives of naturally occurring polymers are employed. It is particularly preferred to use water soluble derivatives of chitosan, the latter being the deacylation product of chitin and being itself water insoluble. Chitin is a natural substance constituting, for example, the carapace of crustaceans and many insects.

Particularly suitable are hydroxyalkylchitosans and carboxyalkylchitosans. Hydroxy-alkylchitosans include chitosans which are derivatized with $C_{1-6}$ alkyl groups possessing 1 to 3 hydroxy groups. As an example, hydroxypropylchitosan may be mentioned. Carboxymethylchitosans include chitosans which are derivitized with $C_{1-6}$ alkyl groups possessing 1 to 3 carboxy groups. As an example, carboxymethylchitosan can be mentioned.

The water soluble film forming agent (component b)) can be used in any amount as long as the formation of a film of the claimed composition can be provided. Typically, the amount of component b) is in the range of 0.1 to 10 wt. %, more preferably 0.3 to 8 wt. %, most preferably 0.5 to 5 wt. % by weight of the total composition.

The composition in accordance with the present invention further comprises usually as a component c) at least one physiologically acceptable solvent. The solvent is typically a water based solvent in order to avoid a frequent and repeated exposure of the nails and the adjacent skin to aggressive organic solvents. Thus, the physiologically acceptable solvent includes water and mixtures of water with co-solvents.

The co-solvent which can be used in combination with water in the composition in accordance with the present invention is not particularly critical but is selected from the usual physiologically safe organic solvents known in the art. Typically, the co-solvent is a hydrophilic solvent and it is preferably selected from alcohols.

Suitable alcohols are branched or linear alcohols having 1 to 3 hydroxy groups and 2 to 6 carbon atoms whereby the hydroxy groups may be partially converted to ethers. Particularly suitable alcohols are ethanol, 1-propanol, 2-propanol (isopropanol). Particularly suitable are ethanol or isopropanol. Preferably, the total amount of co-solvent used in combination with water present in the composition in accordance with the present invention is sufficiently volatile to provide acceptable drying times of the nail varnish. Usual drying times, i.e. the time taken to be dry by touch, are less than about five minutes, preferably less than about two minutes.

When water is used in combination with one or more co-solvents, it is important that the individual solvents are compatible with each other and form a clear solution which is stable against phase separation over time. Moreover, the solvent systems used in accordance with the present invention should not only provide uniform evaporation rates and good stability but also enable good flow viscosity characteristics in order to ease the application of the nail varnish.

The at least one physiologically acceptable solvent (component c)) is usually employed in an amount suitable in order to impart the above noted properties. It is preferred that the component c) is present in the composition in accordance with the present invention in an amount of 40 to 99.8 wt. %, more preferably 60 to 99 wt. %, most preferably 80 to 95 wt. % by weight of the total composition. The water content in component c) is typically 5 to 60 wt. %, preferably 10 to 40 wt. % by weight of component c) in order to impart the desired properties. Consequently, the co-solvent used in combination with water is typically present in an amount of 20 to 95 wt. %, preferably 60 to 90 wt. % by weight of component c) in order to impart the above noted properties.

The composition in accordance with the present invention may further contain other active agents beside the antimycotic agent, e.g. antibiotic agents, antiinflammatory agents, antiseptic agents and/or local anesthesic agents.

Examples of antibiotic agents which may be listed in the composition in accordance with the present invention include amoxicillin, ampicillin, benzylpenicillin, cefaclor, cefadroxil, cefalexin, chloramphenicol, ciprofloxacin, clavulanic acid, clindamycin, doxycyclin, enoxacin, flucloxacillin, kanamycin, lincomycin, minocyclin, nafcillin, nalidixic acid, neomycin, norfloxacin, ofloxacin, oxacillin, phenoxymethylpenicillin, tetracyclin and meclocycline sulfosalicylate.

These antibiotic agents may be used in the respective amounts customary in the art. The antibiotic agents are usually employed in an amount from 0.1 to 10 wt. %.

The antiinflammatory agent which may be used in the composition in accordance with the present invention include steroidal and nonsteroidal antiinflammatory agents.

Examples of steroidal antiinflammatory agents include 21-acetoxypregnenolone, alclometasone or its dipropionate salt, algestone, amcinonide, beclomethasone or its dipropionate salt, betamethasone and salts thereof, including, for example, betamethasone benzoate, betamethasone dipropionate, betamethasone sodium phosphate, betamethasone sodium phosphate and acetate, and betamethasone valerate; clobetasol or its propionate salt, clocortolone pivalate, hydrocortisone and salts thereof, including, for example, hydrocortisone acetate, hydrocortisone butyrate, hydrocortisone cypionate, hydrocortisone phosphate, hydrocortisone sodium phosphate, hydrocortisone sodium succinate, hydrocortisone tebutate and hydrocortisone valerate; cortisone acetate, desonide, desoximetasone, dexamethasone and salts thereof, for example, acetate and sodium phosphate; diflorasone diacetate, fludrocortisone acetate, flunisolide, fluocinolone acetonide, fluocinonide, fluorometholone, flurandrenolide, halcinonide, medrysone, methylprednisolone and salts thereof, e.g. acetate, sodium succinate; mometasone furoate, paramethasone acetate, prednisolone and salts thereof, e.g., acetate, diethylaminoacetate, sodium phosphate, sodium succinate, tebutate, trimethylacetate; prednisone, triamcinolone and derivatives thereof, e.g. acetonide, benetonide, diacetate, hexacetonide.

Examples of nonsteroidal antiinflammatory agents include acetylsalicylic acid, indomethacin, suprofen, phenylbutazone, sulindac, ibuprofen, naproxen, ketoprofen, flurbiprofen, piroxicam and diclofenac.

These antiinflammatory agents may be used in the respective amounts customary in the art. The antiinflammatory agents are usually employed in an amount from 0.1 to 5 wt. %.

Examples of antiseptic agents which may be used in the composition in accordance with the present invention include benzalkoniumchlorid, benzethoniumchlorid, cetrimoniumbromid, chlorhexidin, dequaliniumchlorid, triclocarban, triclosan, salicylic acid, benzoic acid and their salts, p-hydroxybenzoic acid and its esters.

These antiseptic agents may be used in the respective amounts customary in the art. The antiseptic agents are usually employed in an amount from 0.01 to 5 wt. %.

Examples of local anesthesic agents which may be used in the composition in accordance with the present invention include benzocaine, butamben and its picrate, piperocaine hydrochloride, oxybuprocaine hydrochloride, tetracaine hydrochloride, lidocaine hydrochloride, cinchocaine hydrochloride, oxetacaine, propipocaine hydrochloride, bupivacaine hydrochloride, mepivacaine hydrochloride, dyclonine hydrochloride, fomocaine hydrochloride, quinisocaine hydrochloride, polydocanol and benzyl alcohol.

These local anesthestic agents may be used in the respective amounts customary in the art. The local anesthetic agents are usually employed in an amount from 0.3 to 10 wt. %.

In addition, the composition in accordance with the present invention may contain other conventional additives customarily present in cosmetic or medicinal nail lacquers, in particular penetration enhancers. Penetration enhancers include any compound known in the art which can enhance the penetration of the pharmacologically active compound through the skin or through the nail. In other words, the penetration enhancer improves the deep diffusion of the drug. Suitable penetration enhancers include ethyl acetate, dimethyl sulphoxide (DMSO), dimethylacetamide and the penetration enhancers disclosed in WO 99/39680. Ethyl acetate is particularly preferred.

The penetration enhancers may be used in an amount of 0 to 10 wt. %, preferably 0.1 to 8 wt. %, most preferably 1 to 5 wt. % by weight of the total composition.

As a further auxiliary agent, the composition in accordance with the present invention may contain cetyl stearylic alcohol. The presence of cetyl stearylic alcohol has been found to effectively prevent possible crystallization of the antimycotic agent. The crystallization of the antimycotic agent is not desired for aesthetic reasons since the formation of white stains in the nail varnish occurs. More importantly, the bioavailability of the antimycotic agent will be drastically reduced if the antimycotic agent crystallizes out.

It is preferred to use cetyl stearylic alcohol in an amount of 0 to 5 wt. %, more preferably 0.1 to 3 wt. %, most preferably 0.5 to 1.5 wt. % by weight of the total composition.

Other conventional additives customarily present in cosmetic or medicinal nail lacquers may include sedimentation retarders, chelating agents, antioxidants, silicates, aroma substances, wetting agents, lanolin derivatives, light stabilizers and antibacterial substances.

The composition in accordance with the present invention may be prepared according to typical procedures normally employed in the nail varnish field. Specifically, the at least one antimycotic agent and the at least one water soluble film forming agent may be brought into contact with a solvent or mixture of solvents and other liquid components either simultaneously or separately by normal mixing techniques. No particular order of addition of the respective ingredients is required. It is preferred to provide stirring in order to ensure complete dissolution of the ingredients. If any of the ingredients is in the solid form, it is particularly preferred to add such an ingredient gradually to the liquid components in order to prevent clumping.

The composition in accordance with the present invention is applied as a film on the nail in order to prevent and/or treat onychomycoses and other fungal nail diseases. Usually, the nail varnish will be applied repeatedly over a period of several weeks or several months, depending on the severity of the infection, the amount of active agent and the condition of the nails of the patient. The nail varnish may also be prophylactically applied repeatedly to prevent onychomycoses and other fungal nail diseases. The antimycotic agent penetrates well into the weft of the nail and the derma and cannot easily be withdrawn. Therefore, application of the antimycotic nail varnish does not need to be repeated very frequently. Generally the applied nail varnish will contain sufficient active principle to be diffused into the nail and the derma so that the application of the antimycotic should be repeated only once or twice per day in order to ensure its effectiveness.

The preferred film forming agents of the present invention do show a surprising synergistic effect when employed with antimycotic agents. This effect is in particular pronounced with hydroxyalkylchitosans and carboxyalkylchitosans. Further this effect is in particular present when ciclopirox or a salt thereof is used as an antimycotic agent.

While the film forming agents themselves do not show an antimycotic effect when tested in appropriate systems, the effect of the antimycotic agent itself, preferably ciclopirox, is enhanced when employed in combination with the film forming agents in the present invention.

The following examples illustrate the composition of the present invention and its use as a nail varnish. All amounts in "%" are wt. %.

EXAMPLE 1

A nail lacquer composition as shown below was prepared containing 8% ciclopirox in the lacquer formulation.

| | |
|---|---|
| Ciclopirox | 8 g |
| Ethanol 95% | 73 g |
| Depurated water | 13 g |
| Ethyl acetate | 4 g |
| Hydroxypropylchitosan | 1 g |
| Cetyl stearylic alcohol | 1 g |
| | 100 g |

The formulation was prepared by using a suitable closed vessel provided with a stirrer. To this vessel were added ethanol, deionized water and ethyl acetate to form a mixture. Thereafter, cetyl stearylic alcohol and, after dissolution thereof, ciclopirox were added. Finally, hydroxypropylchitosan was added and the resulting mixture was stirred for 24 hours or until dissolution.

The obtained nail lacquer composition had a clear and homogenous appearance even after prolonged storage. Moreover, the lacquer was able to form a matte, non-sticky and plastic film which could strongly adhere to the nails. When applied, the moisture and air permeable lacquer did not burn or cause irritation on the adjacent skin or the periungueal bed.

EXAMPLE 2

A nail lacquer composition as shown below was prepared containing 8% ciclopirox olamine in the lacquer formulation.

| | |
|---|---|
| Ciclopirox olamine | 8 g |
| Ethanol | 57 g |
| Depurated water | 33 g |
| Hydroxypropylchitosan | 1 g |
| Cetyl stearylic alcohol | 1 g |
| | 100 g |

The composition was prepared as shown in Example 1 and the resulting nail lacquer exhibited the same properties as mentioned in Example 1.

EXAMPLE 3

A nail lacquer composition as shown below was prepared containing 5% amorolfine base hydrochloride in the lacquer formulation.

| | |
|---|---|
| Amorolfine base hydrochloride | 5% |
| Hydroxypropylchitosan | 1% |
| Ethanol | 70% |
| Ethyl acetate | 4% |
| Cetyl stearylic alcohol | 1% |
| Depurated water to make | 100% |

The composition was prepared as shown in Example 1 and the resulting nail lacquer exhibited these same properties as mentioned in Example 1.

EXAMPLE 4

A nail lacquer composition as shown below was prepared containing 8% ciclopirox in the lacquer formation.

| | |
|---|---|
| Ciclopirox | 8% |
| Carboxymethylchitosan | 1% |
| Ethanol | 60% |
| Ethyl acetate | 2% |
| Cetyl stearylic alcohol | 0.5% |
| Depurated water to make | 100% |

The composition was prepared as shown in Example 1 and the resulting nail lacquer exhibited the same properties as mentioned in Example 1.

EXAMPLE 5

A nail lacquer composition as shown below was prepared containing 8% ciclopirox and 2% lidocaine hydrochloride monohydrate in the lacquer formulation.

| | |
|---|---|
| Ciclopirox | 8% |
| Lidocaine hydrochloride monohydrate | 2% |
| Hydroxypropylchitosan | 1% |
| Ethanol | 70% |
| Ethyl acetate | 4% |
| Cetyl stearylic alcohol | 1% |
| Depurated water to make | 100% |

The composition was prepared as shown in Example 1 and the resulting nail lacquer exhibited the same properties as mentioned in Example 1.

EXAMPLE 6

A nail lacquer composition as shown below was prepared containing 8% cyclopirox and 1.46% meclocycline 5-sulfosalicylate in the lacquer formulation.

| | |
|---|---|
| Ciclopirox | 8% |
| Meclocycline 5-sulfosalicylate | 1.46% |
| Hydroxypropylchitosan | 1% |
| Ethanol | 70% |
| Ethyl acetate | 4% |
| Cetyl stearylic alcohol | 1% |
| Depurated water to make | 100% |

The composition was prepared as shown in Example 1 and the resulting nail lacquer exhibited the same properties as mentioned in Example 1.

EXAMPLE 7

A nail lacquer composition as shown below was prepared containing 8% ciclopirox, 0.15% dexamethasone phosphate disodium salt and 0.5% neomycin sulfate in the lacquer formulation.

| Ciclopirox | 8% |
|---|---|
| Dexamethasone phosphate disodium salt | 0.15% |
| Neomycin sulfate | 0.5% |
| Hydroxypropylchitosan | 1% |
| Ethanol | 70% |
| Cetyl stearylic alcohol | 1% |
| Isopropanol | 5% |
| Depurated water to make | 100% |

EXAMPLE 8

A nail lacquer composition as shown below was prepared containing 0.2% miconazole nitrate in the lacquer formulation.

| Miconazole nitrate | 0.2% |
|---|---|
| Hydroxypropylchitosan | 1% |
| Ethanol | 73% |
| Ethyl acetate | 4% |
| Cetyl stearylic alcohol | 1% |
| Depurated water to make | 100% |

The composition was prepared as shown in Example 1 and the resulting nail lacquer exhibited the same properties as mentioned in Example 1.

EXAMPLE 9

Penetration Studies

The ciclopirox containing lacquer according to Example 1 was applied on the finger nails of three adult volunteers and the concentration of the active ingredient in the nail was measured by comparing the values for the right hand (unwashed) immediately after application with the values for the left hand after washing after 6 hours. The results are illustrated in Table 1. A good penetration into the nails was shown since 18 to 35% of the applied dose of the antimycotic agent was still present in the nails after hand washing after 6 hours. Therefore, it could be shown that the composition in accordance with the invention is suitable as an antimycotic nail varnish even though the film forming agent is water soluble.

EXAMPLE 10

Inhibition of the pathogen responsible for onychomycosis in humans was tested in accordance with standard procedures on standard plates.

Comparison of the antimycotic effect of ciclopirox (8%) alone and, hydroxypropychitosan (1%) alone with the combination of these two compounds (8 and 1%, respectively) with respect to the growth of Tricophytes Mentagrophytes on Sabourand Dex. at 30° C. gave the following results (amounts applied in each case 10, 20 and 30 µl):

| hydroxypropylchitosan: | no inhibition |
|---|---|
| ciclopirox: | good inhibition |
| ciclopirox with hydroxypropylchitosan: | better inhibition than with ciclopirox alone |

TABLE 1

| | CONCENTRATION VALUES (µg/mg of nail) | | | | | | | | |
|---|---|---|---|---|---|---|---|---|---|
| Subject | V01 | | V02 | | V03 | | Mean | | Ratio |
| Hand | Left | Right | Left | Right | Left | Right | Left | Right | % |
| Finger | | | | | | | | | |
| Thumb | 0.39 | 2.06 | 0.97 | 3.98 | 0.46 | 1.74 | 0.61 | 2.59 | 23.39 |
| Index | 0.78 | 4.64 | 1.83 | 3.02 | 0.58 | 2.28 | 1.06 | 3.31 | 32.09 |
| Middle | 0.76 | 4.52 | 0.78 | 5.06 | 0.66 | 2.67 | 0.73 | 4.08 | 17.96 |
| Annular | 1.35 | 5.72 | 3.16 | 5.99 | 1.29 | 4.82 | 1.93 | 5.51 | 35.09 |
| Little | 1.12 | 3.81 | 2.84 | 3.49 | 1.79 | 4.71 | 1.92 | 7.34 | 26.12 |

Note: left hand had been washed after 6 hours from application of the lacquer

The invention claimed is:

1. A nail varnish composition comprising a composition, wherein said composition comprising
   a) at least one antimycotic agent and
   b) at least one water soluble agent,
      wherein component b) is a derivative of chitosan selected from hydroxyalkylchitosans or carboxyalkylchitosans, and wherein said at least one water soluble agent differs from said at least one antimycotic agent
   wherein component a) is present in an amount of 0.1 to 15 wt. %, and
   wherein component a) is selected from 1-hydroxy-2-pyridone compounds, imidazole derivatives, polyene derivatives, allylamine derivatives, triazole derivatives, morpholine derivatives, griseofulvin compounds, undecylenic acid or salts thereof, tolnaphtate, fucytosine or salts thereof.

2. The composition according to claim 1, wherein component a) is ciclopirox or a salt thereof.

3. The composition according to claim 1, wherein component b) is present in an amount of 0.1 to 10 wt. %.

4. The composition according to claim 1, wherein component b) is hydroxypropylecitosan.

5. The composition according to claim 1, further comprising c) at least one physiologically acceptable solvent.

6. The composition according to claim 1, wherein component a) is selected from 1-hydroxy-2-pyridone compounds, imidazole derivatives, polyene derivatives, allylamine derivatives, triazole derivatives, morpholine derivatives, griseofulvin compounds, undecylenic acid or salts thereof, tolnaphtate, flucytosine or salts thereof.

7. The composition according to claim 1, wherein component a) is ciclopirox or a salt thereof.

8. The composition according to claim 1, wherein component a) is ciclopirox or a salt thereof.

9. The composition according to claim 1, wherein component b) is present in an amount of 0.1 to 10 wt. %.

10. The composition according to claim 1, wherein component b) is present in an amount of 0.1 to 10 wt. %.

11. The composition according to claim 1, wherein component b) is hydroxypropylchitosan.

12. The composition according to claim 1, wherein component b) is hydroxypropylchitosan.

13. The composition according to claim 1, further comprising c) at least one physiologically acceptable solvent.

14. The composition according to claim 1, further comprising c) at least one physiologically acceptable solvent.

15. The composition according to claim 2, further comprising c) at least one physiologically acceptable solvent.

16. The composition according to claim 3, further comprising c) at least one physiologically acceptable solvent.

17. The composition according to claim 1, wherein component a) is Miconazole or a salt thereof.

18. The composition according to claim 1, wherein component a) is Amorolfine or a salt thereof.

19. The composition according to claim 1, wherein component a) is Terbinafine or a salt thereof.

* * * * *

UNITED STATES PATENT AND TRADEMARK OFFICE
CERTIFICATE OF CORRECTION

PATENT NO. : 7,033,578 B2
APPLICATION NO. : 10/297345
DATED : April 25, 2006
INVENTOR(S) : Mailland It is certified that error appears in the above-identified patent and that said Letters Patent is hereby corrected as shown below:

IN THE CLAIMS:

Claim 1, column 10, lines 52 - 53, "fucytosine" should read --flucytosine--.

Claim 4, column 10, line 59, "hydroxypropylecitosan" should read --hydroxypropylchitosan--.

Signed and Sealed this

Twenty-fifth Day of July, 2006

JON W. DUDAS
*Director of the United States Patent and Trademark Office*